United States Patent [19]

Tacke et al.

[11] Patent Number: 5,734,070
[45] Date of Patent: Mar. 31, 1998

[54] HARDENING OF UNSATURATED FATS, FATTY ACIDS OR FATTY ACID ESTERS

[75] Inventors: Thomas Tacke, Friedrichsdorf; Stefan Wieland, Offenbach; Peter Panster, Rodenbach; Martin Bankmann, Gelnhausen; Reinhold Brand, Glenhausen; Hendrik Mägerlein, Kronberg, all of Germany

[73] Assignee: Degussa Aktiengesellschaft, Frankfurt am Main, Germany

[21] Appl. No.: 689,836

[22] Filed: Aug. 14, 1996

Related U.S. Application Data

[63] Continuation of PCT/EP95/00456 Feb. 9, 1995.
[51] Int. Cl.$^6$ .................................................. C07C 31/56
[52] U.S. Cl. .................................................. 554/144
[58] Field of Search ................................. 554/144

[56] References Cited

U.S. PATENT DOCUMENTS 4,847,016  7/1989  Göbel ..................................... 554/144

FOREIGN PATENT DOCUMENTS 9406738  3/1994  WIPO .
9411472  5/1994  WIPO .

*Primary Examiner*—Allen J. Robinson
*Assistant Examiner*—Mary C. Cebulak
*Attorney, Agent, or Firm*—Beveridge, Derandi, Weilacher & Young, L.L.P.

[57] ABSTRACT

A process is disclosed for continuously hydrogenating unsaturated fats, fatty acids or fatty acid esters on a shaped catalyst in a solid bed. The reactants flow over the catalyst in the presence of a medium or solvent mixture in supercritical conditions. This leads to considerably improved activity and selectivity of the hydrogenation reaction compared with conventional trickle bed hydrogenation processes.

10 Claims, 1 Drawing Sheet

HARDENING OF UNSATURATED FATS, FATTY ACIDS OR FATTY ACID ESTERS

REFERENCE TO RELATED APPLICATION

This is a continuation of PCT/EP 95/00456 filed Feb. 9, 1995 which is relied upon and incorporated herein by reference.

BACKGROUND OF THE INVENTION

The present invention relates to a method of the continuous hardening of unsaturated fats, fatty acids or fatty acid esters on a shaped catalyst in the fixed bed.

Renewable fats or oils of animal or vegetable origin come under the triglycerides. They form an essential ingredient of human food. Free fatty acids can be obtained by splitting of the triglycerides into fatty acids and glycerol. The fatty acids from vegetable or animal sources have chain lengths of 12 to 30 carbon atoms. Unsaturated fatty acids with up to three double bonds are mostly involved. The double bonds, in particular in triply unsaturated fatty acids, are the reason for the low thermal stability and easy oxidation of the unsaturated fatty acids.

Polyunsaturated fats are particularly important for human food, however it is frequently necessary, in order to improve the shelf life and to improve the handling properties of these fats, to hydrogenate the double bonds of the polyunsaturated fatty acids selectively down to one double bond. This is then termed "selective hardening". Natural fats exist almost completely in the cis-isomeric form. Trans-isomeric fats are of less value physiologically. They are suspected, together with the through-hardened fats, of increasing the triglyceride or cholesterol level in human blood. The aim of the selective hardening of fats is therefore to suppress the formation of trans-isomers as well as the formation of completely through-hardened fats.

For applications in industry the double bonds must be removed as completely as possible by hydrogenation, with simultaneous maintenance of the acid character of the fatty acids. This complete hydrogenation of the double bonds of fatty acids is also referred to as through-hardening of the fatty acids.

The degree of saturation of fats and fatty acids, i.e. their content in still remaining double bonds, can be determined by the iodine value Tgl-64 (Wijs method) of the A.O.C.S. Natural fats possess, depending on the degree of saturation, iodine values between 150 (soybean oil) and 50 (beef fat).

Fats and fatty acids are still hydrogenated mainly batch-wise at temperatures of 100°–300° C. under an increased hydrogen pressure of 1–35 bar in the presence of a suitable catalyst. Use is mainly made for this purpose of nickel catalysts in the form of finely-divided nickel either directly or on silicon oxide as a support. In addition to these nickel catalysts, however, supported noble metal catalysts are also known for the selective or complete hardening of fats, fatty acids and fatty acid esters. Supported noble metal catalysts are suitable in particular for the continuous hardening of fats and fatty acids in trickle bed reactors.

Thus e.g. DE 41 09 502 describes the continuous hardening of untreated fatty acids in the trickle bed on a palladium/titanium oxide catalyst. The reaction media are here reacted in the form of a 2-phase mixture of liquid fatty acids and hydrogen gas on the fixed bed catalyst. The hydrogenating activity in this method permits space velocities of only 1.2 $h^{-1}$ and should be improved in the interests of higher economic returns. It has been found in addition that the selective hardening in the trickle bed tends towards the formation of trans-isomers.

The object of the present invention is therefore to indicate a method of the continuous hardening of fats, fatty acids and fatty acid esters which exhibits a substantially improved hydrogenating activity. The method is intended to be suitable both for the selective hardening of edible fats and oils with low trans-isomer formation and for the complete hardening of fats and free fatty acids for industrial applications.

The object is achieved by a method for the continuous hardening of unsaturated fats, fatty acids or fatty acid esters on a shaped catalyst in the fixed bed, which is characterized in that the fats, fatty acids or fatty acid esters are together with the hydrogen required for the hardening and in the presence of a supercritical solvent medium or solvent conveyed over a catalyst and in so doing converted and that the fats, fatty acids or fatty acid esters are then separated from the supercritical solvent medium by expansion and are therefore present as pure substance without solvent.

Supercritical solvents or media are used in many areas of industrial chemistry and also of food chemistry. The main area of use of supercritical media in food chemistry is the extraction of particular food components from natural raw material sources. Use is preferably made for the latter of supercritical carbon dioxide, which is distinguished by high purity, good environmental compatibility and relatively low costs. The hardening of fats, fatty acids or fatty acid esters in supercritical solvent media has not become known yet to date.

The method according to the invention leads to surprisingly high hydrogenating activities of the catalysts used. It has been found that the hydrogenating activities of similar types of catalysts, when used in the method according to the invention, can be greater by a factor of 10 to 50 than when used in the conventional trickle bed hardening. In addition the method according to the invention exhibits a lower cis/trans-isomerization.

SUMMARY OF THE INVENTION

The method works particularly advantageously with reaction temperatures between the critical temperature $T_{cr}$ of the solvent and ten times the value, preferably between $T_{cr}$ and $7 \times T_{cr}$, and at pressures between 0.8 times the pressure $P_{cr}$ of the solvent at the critical point and $6P_{cr}$, preferably between $P_{cr}$ and $4 \times P_{cr}$.

Suitable solvents for the method according to the invention are acetone, ammonia, butane, carbon dioxide, chloroform, chlorotrifluoromethane, dichlorodifluoromethane, dichlorofluoromethane, 1,2-dichlorotetrafluoroethane, ethane, ethyl methyl ether, methane, nitrogen monoxide, dinitrogen monoxide, n-pentane, propane, sulphur hexafluroide, trichlorofluoromethane and xenon. By means of binary or ternary mixtures of these solvents, the solvent properties can be adjusted to the substance to be dissolved. A further raising of the solvent power and the selectivity of the solvent properties of supercritical solvents can be achieved by the addition of small amounts (up to approx. 2 vol. %) of so-called modifiers. There are suitable as modifiers alcohols (methanol, ethanol), aldehydes, ketones, acids, hydrocarbons as well as fluorinated/chlorinated hydrocarbon and water.

Particularly suitable are solvents or solvent mixtures whose critical temperature lies in the range between −120° C. and 250° C. at critical pressures between 20 and 200 bar and which exhibit a density at the critical point of more than 0.1 g/cm$^3$.

Preferentially suitable are carbon dioxide, nitrogen monoxide, dinitrogen monoxide, propane and pentane with densities at the critical point of between 0.2 and 0.5 g/cm$^3$. They exhibit a good solvent power for organic materials. Under the reaction conditions of the method the densities of the supercritical solvent media increase significantly with rising pressure in the reactor. Their solvent power thereby undergoes a further improvement. In the case of carbon dioxide, for example, the density doubles from some 0.5 g/cm$^3$ to some 1 g/cm$_3$ if the pressure is raised from $P_{cr}$ to 5×$P_{cr}$ (at the critical temperature in each case).

The critical temperatures lie between −94° C. for nitrogen monoxide and 196.5° C. for pentane and thus permit a particularly gentle handling of organic materials. Preferably used are carbon dioxide with a critical temperature of 31° C., a critical pressure of 72.8 bar and a critical density of 0.467 g/cm$^3$ and dinitrogen monoxide with a critical temperature of 36.4° C., a critical pressure of 71.5 bar and a critical density of 0.452 g/cm$^3$. The solvent properties of carbon dioxide can be enhanced by mixing with propane (e.g. mixture of 75 parts by volume of carbon dioxide and 25 parts by volume of propane).

Use can be made for the method according to the invention of all known hydrogenating catalysts, i.e. also e.g. nickel, platinum, palladium, rhodium, ruthenium catalysts or combinations thereof on $SiO_2$, $Al_2O_3$, $TiO_2$, $ZrO_2$, MgO, activated carbon or on mixtures thereof such as e.g. MgO× $Al_2O_3$. The platinum group metals on shaped supports have proved particularly effective. The catalytic activity can be influenced by promoters. Thus it is known e.g. that silver as a promoter for nickel and palladium catalysts reduces the formation of trans-isomers. Sulphidized nickel catalysts in particular are used in engineering.

The supports should have a high specific surface in order to permit good dispersion of the catalyst metals. Advantageous are specific surfaces between 10 and 1000 m$^2$/g. Particularly important for the method according to the invention is also the pore structure of the supports. They should have a total pore volume between 0.05 and 6.5 ml/g, which is composed predominately of meso- and macropores. Micropores are undesirable and should make up only a small percentage of the total pore volume.

The terms micro-, meso and macropores are used here in conformity with the definitions of the IUPAC. According to these definitions the pore groups incorporate the following diameter ranges:

Micropores: d<2nm

Mesopores: d=2 . . . 50 nm

Macropores: d>50 nm

Meso- and macropores guarantee through their large pore diameters optimal accessibility to the catalytically active noble metal crystals deposited on their surfaces for the fat, fatty acid or fatty acid ester molecules. This accessibility is supported by the fact that the supercritical solvents used had a low viscosity.

The content in platinum group metals on the support should come to between 0.05 and 5 wt %, preferably between 0.1 and 3.0 wt %.

The platinum group metals must be deposited finely distributed on the support, in order to provide as great a metal surface as possible for the catalytic process. A measure of the size of the catalytically active metal surface is the adsorption of carbon monoxide. The latter should be, as a function of the content in platinum metal groups, between 0.05 and 5.0 ml CO/g of the finished catalyst elements. If it is assumed that one noble metal atom adsorbs one CO molecule and the latter behaves like an ideal gas with an assumed projected area of 6.25×10$^{-20}$ m$^2$/molecule, there can be calculated from the above-mentioned values an active surface of the platinum group metals on the finished catalyst of approx. 0.1–10 m$^2$/g.

The catalyst supports can be of any shape. There are suitable in particular all shapes known for fixed bed catalysts, namely spheres, cylinders, hollow cylinders and open wheels as well as monolithic catalyst supports in the form of honeycomb elements with parallel flow channels or foam ceramics with an open pore system. The monolithic honeycomb elements can consist throughout of the high-surface support material (solid catalyst) or be composed of an inert support element with a coating of the high-surface support material (coating catalyst).

It is a particular advantage of the method according to the invention that compared with conventional methods small-sized catalyst supports can be used as support material, without the pressure loss through the catalyst bed becoming too great.

This is made possible by the low viscosity of the supercritical solvent. With advantage, therefore, catalyst supports can be used with outer dimensions in the range between 0.1 and 3.0 mm, in particular between 0.2 and 1.0 mm. Very high catalyst activities can be achieved in this way. Spherical-shaped supports are preferred.

Because of the small dimensions of the catalysts, the latter exhibit in the bed a very high geometric surface relative to the total volume of the bed. This benefits the catalytic activity of the catalyst bed. This activity can be further improved if the platinum group metals are deposited on these supports in an outer shell of 10–40 µm. The shell impregnation is of importance particularly for the selective fat hardening. Specifically, it prevents fat molecules which are diffused into the interior of the catalyst support from making protracted contact there with catalytically active metals and hence being fully through-hardened. For the complete hardening of fats or fatty acids use can conversely also be made of fully through-impregnated catalyst supports.

Various materials are suitable as catalyst supports. The materials must however satisfy the above-mentioned requirements as regards their physical properties and be resistant to the reaction media, in particular to the fatty acids. For the conventional fat hardening, activated carbon, silicon dioxide, aluminum oxide, mixed aluminum/silicon oxides, barium sulphate, titanium oxide, glass beads coated with titanium oxide and ion-exchange resins have proved satisfactory. These support materials can also be used in the method according to the invention. The above-mentioned requirements are however met in an optimal manner by organosiloxane amine copolycondensates or by polymeric, secondary and/or tertiary organosiloxane amine compounds or by organosiloxane polycondensates. These support materials are described in the German patent specifications DE 38 00 563 C1, DE 38 00 564 C1, DE 39 25 359 C1 and DE 39 25 360 C1 which are relied upon and incorporated herein as references and in the as yet unpublished patent application P 42 25 978.1. Platinum group metal-containing catalysts on these supports are disclosed in the patent specifications DE 41 10 705 C1 and DE 41 10 706 C1 which are relied on and incorporated herein as references.

DETAILED DESCRIPTION OF THE PREFERRED EMBODIMENTS

Figure 1:
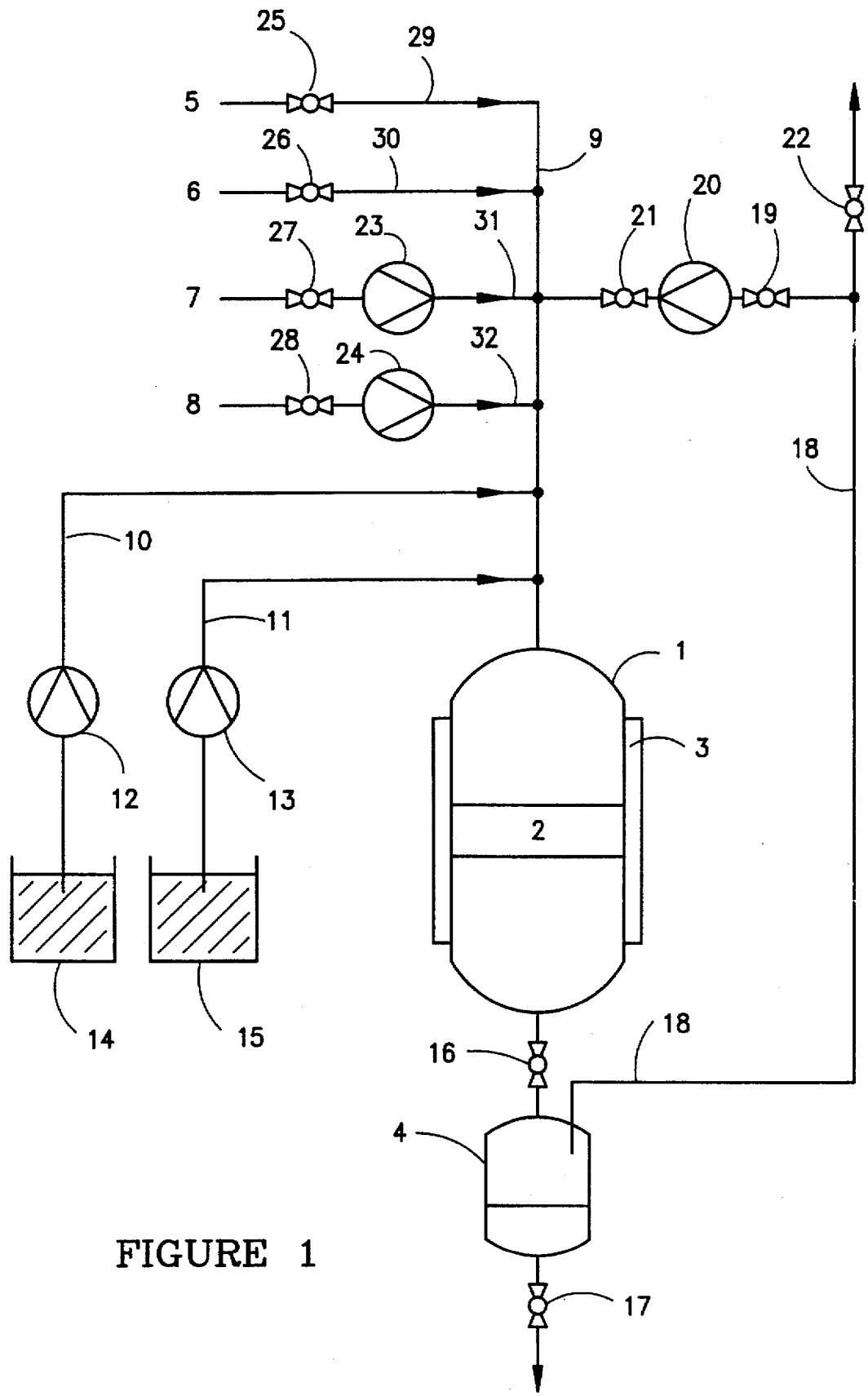
FIG. 1 is a schematic diagram of the catalytic hydrogenation apparatus.

The following examples make clear the mode of operation of the method according to the invention for the hydrogenation of fats, fatty acids or fatty acid esters.

FIG. 1 shows a diagrammatic view of the hydrogenation apparatus used for the examples. Conventional equipment can be used for the reactor apparatus. Element 1 designates the hydrogenation reactor. An 840 mm long stainless steel tube with an inner bore of 15.7 mm is involved. This stainless steel tube is filled to about half its height with a catalyst layer (2) from 10 to 30 mm in height. Above and below the catalyst bed are located plugs of quartz wool. They separate the actual catalyst bed from glass beads which occupy the remaining free volume of the stainless steel tube above and below the catalyst bed. The inert bed above the catalyst bed serves at the same time for mixing the supercritical medium or solvent with the reactants.

The reactor possesses an outer jacket (3), through which, for the setting of the reaction temperature, silicone oil flows in countercurrent as a heating medium. This arrangement guarantees that the temperature gradient through the catalyst bed is very small.

The supercritical solvent medium, such as carbon dioxide, required for the method is fed to the reactor from transfer line (7), through valve (27) by pump (23) into line (31) and then into line (9). Additional supercritical solvent medium, such as propane, can be fed to the reactor from transfer line (8), through valve (28) by pump (24) into line (32) and then into line (9). Nitrogen is fed from transfer line (6), through valve (26) into line (30) and from there on into line (9) and into the reactor (1). Nitrogen is used simply for the cleaning of the reactor before and after a hydrogenation. Hydrogen is introduced into the supercritical solvent media from line (5). The hydrogen enters through valve (25) into line (29) which connects to line (9). There are also charged to the supercritical mixture of hydrogen, carbon dioxide and optionally propane above the reactor any modifier (14) required and the educt (15) to be hydrogenated. The modifier (14) is pumped by (12) into line (10) which connects to line (9). The educt (15) is pumped by (13) into line (11) which connects to line (9).

In contrast to the conventional trickle bed method, the vertical arrangement of the reactor tube selected here is not mandatory. In one possible embodiment of the method there exists with adequate dilution of the reactants in the supercritical medium or solvent a virtually homogeneous phase, which may be pumped over the catalyst bed at any orientation of the reactor tube. The vertical arrangement was selected here merely to simplify the description.

After passage through the reactor the reaction media enter a separator (4) through valve (16). In this separator the reaction mixture of product, optionally surplus hydrogen and supercritical solvent is converted into a two-phase mixture by expansion to pressures below the critical pressure. During the expansion the solvent and the hydrogen pass into the gaseous state, whereby the solvent power of the solvent is reduced to practically zero. The product of the hydrogenation reaction therefore precipitates out of the reaction mixture as a liquid or solid and can therefore be separated from the gaseous solvent and the remaining hydrogen through valve (17). The now gaseous solvent and the remaining hydrogen can either be released through line (18) and valve (22) to the atmosphere or can pass through valve (19) to be compressed again by pump (20) and recycled into the process through valve (21). The expansion of the reaction medium after passage through the reactor can also be carried out in a plurality of stages with pressure reduction. The reaction products can consequently be precipitated in a plurality of fractions, depending on solubility in the supercritical medium An optionally necessary substance separation, e.g. by distillation, can therefore be dispensed with.

The hydrogenation apparatus of FIG. 1 was used in the following examples for the continuous hydrogenation of ethyl esters of various fatty esters, whose main constituent was linoleic acid ethyl ester. The educt had the following detailed composition:

The hydrogenation apparatus of FIG. 1 was used in the following examples for the continuous hydrogenation of ethyl esters of various fatty esters, whose main constituent was linoleic acid ethyl ester. The educt had the following detailed composition:

TABLE 1

| Composition of the educt | | | |
|---|---|---|---|
| Linoleic acid ethyl ester | C18:2: | 76.8 | wt % |
| Oleic acid ethyl ester | | | |
| cis-form | C18:1(c): | 13.2 | wt % |
| trans-form | C18:1(t): | 0 | wt % |
| Stearic acid ethyl ester | C18:0: | 2.7 | wt % |
| Palmitic acid ethyl ester | C16:0: | 7.3 | wt % |

Pure carbon dioxide or a carbon dioxide-propene gas mixture was used as the supercritical solvent media.

Linoleic acid ethyl ester is an ester of the doubly unsaturated linoleic acid with 18 carbon atoms.

The double bonds of this fatty acid are hydrogenated in a consecutive reaction, i.e. after one another. There are therefore contained in the reaction product, in addition to residues of the linoleic acid C18:2, the monounsaturated oleic acid C18:1 and the completely saturated stearic acid C18:0. The monounsaturated oleic acid can be present in two isomeric forms, namely as cis-form C18:1(c) and as trans-form C18:1(t). Oleic acid from natural sources exhibits predominantly the cis-form. During the hydrogenation the oleic acid is partially isomerized to the trans-form.

For the analysis of the reaction product the liquid was removed hourly from the separator and a sample of the latter examined in a gas chromatograph and the reaction products formed were identified and determined quantitatively. From these measurements it was possible to determine the selectivity of the formation of oleic aid compared with stearic acid and the degree of the cis/trans-isomerisation As a measure of the integral activity (A) of the catalysts in the method according to the invention, there were calculated from the iodine value of the samples; a) the iodine value decease, standardized to one hour, b) the specific iodine value decrease, standardized to one hour and 1 g of active metal, and c) the specific hydrogenating activity in number of moles of hydrogen which were converted per gram of active metal (am) per hour. The iodine value (IV) is a measure of the number of double bonds not yet saturated in the product and is given in grams of iodine which are adsorbed by 100 g of the samples. It is determined according to their official method Tgl-64 (Wijs method) of the A.O.C.S. From the iodine value $IV_{educt}$ of the educt and the iodine number $IV_{product}$ of the product the specific hydrogenating activity A is calculated as:

$$A \frac{(IV_{educt} - IV_{product}) \times \Phi}{100 \times g\,am \times M_{iodine}} \quad \left[ \frac{mol\,H_2}{g\,am \times h} \right]$$

$\Phi$=flow rate of the educt in [g/h]

g am=gram of active metal [g]

$M_{iodine}$=molecular weight of iodine in [g mol]

The specific cis/trans-isomerization B is given dimensionless as percent of trans-isomer in the product formed according to GC analysis in relation to the iodine value decrease.

$$B = \frac{\% \text{ trans-isomer}}{IV_{educt} - IV_{product}}$$

Four different catalyst systems were used, which are given with their properties in Table 2. In the case of the Pd/C catalyst a shell catalyst (20 μm shell) on a mesoporous spherical carbon is involved. Pd/OFP denotes a palladium catalyst on a support of an organofunctional polysiloxane according to Example 2 of patent specification DE 41 10 706 C1 which is relied on and incorporated herein by reference.

There was used as a base metal catalyst the commercial catalyst RCH Ni 55/5 TST of Hoechst. This is a supported catalyst with a content of some 54 wt % of nickel on kieselguhr containing 4 wt % of manganese.

In Table 2 the catalyst systems investigated are characterized by details of the shape and size of the support material and by details of its pore structure. As regards the nickel catalyst, the table contains only the parameters contained in the data sheets.

The pore volumes given in Table 2 were determined in the case of micro- and mesopores by the evaluation of nitrogen adsorption isotherms to DIN 66133. The pore volume of the macropores was determined by Hg porosimetry, likewise to DIN 66133.

Table 2 also contains data on the nature of the distribution of the platinum group metals through the cross-section of the catalyst supports and on the fine-particle character of the platinum group metals measured by their carbon monoxide adsorption.

Pd/polystyrene catalyst (cat. 4) also, activities higher by orders of magnitude are again found in the method according to the invention, but also significantly smaller cis/trans-isomerisations. The Pd/C (cat. 1) and Pt/OFP (cat. 3) catalysts likewise exhibit in the method according to the invention very good activities and selectivities, better than comparable catalysts in the trickle bed hardening (cat. 4–9). These results were moreover also obtained at 60° C., while most the other tests cited were carried out at far higher temperature.

It is known from the literature that platinum is not very suitable as an active component in the hydrogenation of fats, fatty acids and fatty acid esters. It can be seen from Table 3, however, that the Pt/OFP catalyst exhibits perfectly good hydrogenating activities in the presence of a supercritical medium or solvent and is distinguished in particular by a small formation of trans-isomers.

Palladium catalysts are conversely known in the trickle bed hardening for the formation of trans-isomers (see catalysts 4 and 5 in Table 3). In the hydrogenation method according to the invention the formation of trans-isomers is however sharply reduced by the palladium catalysts.

The commercial nickel catalyst (catalyst 10) was used both in the hydrogenation method according to the invention and in the conventional trickle bed method. In the conventional trickle bed method working parameters of 170° C., a hydrogen pressure of 20 bar and a space velocity of 5 h$^{-1}$ were selected. In the method according to the invention the temperature was able to be reduced to 120° C. Despite this, a 25 to 30% higher hydrogenating activity was observed with significantly reduced cis/trans-isomerization.

TABLE 2

Properties of the catalysts:

| Catalyst | Support | Shape | Size [mm] | Pores [ml/g] Micro | Meso | Macro | total | Catalytic metal | Metal distribution | Metal content (%) | CO absorption [ml CO/g cat.] |
|---|---|---|---|---|---|---|---|---|---|---|---|
| Pd/C | C | Spheres | 0.4–0.8 | 0.19 | 0.42 | 0.14 | 0.75 | Pd | 20 μm shell | 0.5 | 0.39 |
| Pd/OFP | OFP | Spheres | 0.3–0.8 | — | 1.54 | 0.72 | 2.26 | Pd | 20 μm shell | 1.0 | 0.65 |
| Pt/OFP | OFP | Spheres | 0.4–0.8 | — | 1.48 | 0.68 | 2.16 | Pt | through-impregnated | 2.0 | 0.22 |
| Ni/SiO$_2$ | SiO$_2$ | Granulate | 0.45–1.0 | | | | 0.5 | Ni | homogeneous | 54 | |

EXAMPLE 1

The educt consisting of ethyl esters of various fatty acids which is characterized in Table 1 was hydrogenated according to the invention in the presence of a supercritical medium with the use of the catalysts of Table 2 in the reaction conditions given in Table 3. The space velocity given in Table 3 (LHSV—liquid hourly space velocity) is the liquid volume of the reaction educt which is metered hourly per catalyst volume.

The results regarding specific hydrogenation activity A, iodine value decrease per hour and the specific cis/trans-isomerization are listed in Table 3. Table 3 also contains a comparison with trickle bed hardenings from various literature sources.

As Table 3 shows, there can be achieved in the presence of a supercritical solvent medium in the hardening of fats and oils, fatty acids or fatty acid esters with suitable catalysts far better activities and also lower cis/trans-isomerisations than in the known continuous trickle bed hardening. Catalyst 2 (Pd/OFP) exhibits, with significantly reduced formation of trans-isomers, 65 times and 292 times better metal-specific hydrogenating activities in Comparison with commercial Pd/C (cat. 5) and Ni/SIO$_2$ (cat. 6) catalysts respectively. As regards the metal-specific iodine value decrease, the factors are 149 and 837 respectively. Compared with the The data in Table 3 demonstrate the advantage of the hydrogenation according to the invention in the presence of supercritical media or solvents. The catalysts on OFP supports with their optimal pore structure lead moreover to particularly good results.

Whereas catalysts 1, 2 and 3 are despite their small particle diameter well suited to industrial applications of the hydrogenation method according to the invention, this is not the case with catalysts 4, 5 and 6 in the conventional trickle bed hardening. Their particle diameters are too small for this method and lead to a high pressure loss in the trickle bed.

Typical particle sizes for the application in the trickle bed therefore amount to 1 to 5 mm and result in a further decline in the specific hydrogenating activity compared with the values of catalysts 4, 5 and 6 in Table 3.

The hydrogenation method according to the invention operates conversely with a reaction mixture consisting of supercritical medium or solvent, hydrogen and the fats, fatty acids or fatty acid esters to be hydrogenated, which possesses by virtue of the supercritical conditions for the solvent a low viscosity and therefore also does not lead to a disproportionately large pressure loss in the catalyst bed with small particle diameters in the range between 0.1 and 1 mm.

TABLE 3

Comparison of various catalyst systems in the supercritical and trickle bed hardening

| Cat. no. | Catalyst designation/particle size | Hydrogenating activity A | IV decrease [l/h] | specific IV decrease [l/h × g am] | cis/trans-isomerisation B | Reaction parameters | Source |
|---|---|---|---|---|---|---|---|
| 1 | 0.5% Pd/C 0.3–0.8 mm | 3.2 | 270 | 46154 | 0.23 | 60° C., 100 bar $CO_2$ + superstoichiometric $H_2$ LHSV 10 $h^{-1}$ | according to invention |
| 2 | 1% Pd/OFP 0.4–0.8 mm | 14.3 | 1151 | 209273 | 0.11 | | |
| 3 | 2% Pt/OFP 0.4–0.8 mm | 1.5 | 230 | 20909 | 0.08 | Linoleic acid ethyl ester | |
| 10 | 54% Ni/SiO$_2$ 0.45–1.0 mm | 0.04 | 512 | 560 | 0.12 | 120° C., 100 bar $CO_2$, LHSV 5 $h^{-1}$ + superstoichiometric $H_2$ linoleic acid ethyl ester | according to invention |
| 10 | 54% Ni/SiO$_2$ 0.45–1.0 mm | 0.03 | 429 | 470 | 0.25 | 170° C., 20 bar $H_2$, LHSV 5 $h^{-1}$ linoleic acid ethyl ester | trickle bed hardening |
| 4 | 4% Pd/polystyrene 0.3–0.8 mm | 0.53 | 270 | 3375 | 0.3 | 100° C., 3.45 bar $H_2$, LHSV 6 $h^{-1}$, soybean oil | JAOCS, Vol. 66 No. 7 |
| 5 | 1% Pd/C 0.18–0.42 mm | 0.22 | 28 | 1400 | 1.5 | 100° C., 3.45 bar $H_2$, LHSV 14 $h^{-1}$, soybean oil | July 1989 |
| 6 | 50% Ni/SiO$_2$ 0.03 mm | 0.049 | 250 | 250 | 0.4 | 150° C., 3.45 bar $H_2$, LHSV 10 $h^{-1}$, soybean oil | |
| 7 | 2% Pd/TiO$_2$ | 0.12 | 57.8 | 2890 | — | 170° C., 20 bar $H_2$, | DE 4109502 |
| 8 | 2% Pd/C | 0.23 | 57.2 | 5720 | — | LHSV 1.07, dist. fatty acid | Degussa AG |
| 9 | 0.5% Pd/Al$_2$O$_3$ | 0.10 | 48 | 9600 | — | 60° C., 21.1 bar $H_2$ LHSV 1 $h^{-1}$ Fatty acid (oleic acid) | DOS 2310985 |

EXAMPLE 2

Using the Pd/OFP catalyst no. 2 of Table 3, a direct comparison was made between the conventional trickle bed hardening and the hardening according to the invention in the presence of a supercritical medium or solvent.

Both tests were carried out under exactly identical reaction conditions in the hydrogenation apparatus described. In order to simulate the conventional trickle bed hardening, the supercritical solvent $CO_2$ was replaced by nitrogen. The space velocity (LHSV) in the tests was 15 $h^{-1}$ in each case. The results are given in Table 4.

The Pd/OFP catalyst also produces very good activities in the conventional trickle bed hardening under increased nitrogen pressure and exhibits a moderate tendency to the formation of trans-isomers. This is due to the good diffusion properties of the OFP support with its pore structure consisting only of meso- and macropores.

However, in the hydrogenation method according to the invention, in the presence of a supercritical medium or solvent, quite significantly better performance data are achieved with the same catalyst.

TABLE 4

Comparison of the hardening method according to the invention under supercritical conditions with the conventional trickle bed hardening

| Cat. no. | Catalyst designation/ particle size | Hydrogenating activity A | IV decrease [l/h] | specific IV decrease [l/h × g am] | cis/trans-isomerisation B | Reaction parameters | Method |
|---|---|---|---|---|---|---|---|
| 2 | 1% Pd/OFP | 22.8 | 1821 | 331091 | 0.078 | 60° C., 100 bar $CO_2$ + stoichiometric $H_2$ LHSV 15 $h^{-1}$ linoleic acid ethyl ester | according to the invention |
| 2 | 1% Pd/OFP | 9.2 | 730.5 | 132818 | 0.226 | see above but $N_2$ instead of $CO_2$ | conventional trickle bed hardening | am = active metal

EXAMPLE 3

In a third test series the dependence of the hydrogenating activity and the cis/trans-isomerization on the space velocity was determined. Table 5 contains the results for the space velocities (LHSV) 5, 10, 15, 30 and 60 $h^{-1}$.

Conventional trickle bed hardenings are diffusion-limited, i.e. the hydrogenation ability is limited by the diffusion velocity of the reactants towards the catalytically active centres and away from them. A raising of the space velocity therefore does not lead to a stronger catalytic reaction. The results of Table 5 show conversely that the hydrogenation method according to the invention is still controlled kinetically even at space velocities of 60 $h^{-1}$, i.e. the catalytic reaction is not limited by diffusion processes in the catalyst, but simply depends on the velocity at which the reaction mixture is fed to the catalyst bed.

The catalyst activity therefore increases linearly with rising space velocity. Parallel with this a reduced formation of trans-isomers is observed.

Above a space velocity of 15 $h^{-1}$ the catalyst activity no longer increases linearly but still increases significantly. At the same time slightly more trans-isomers are formed.

hardening, catalysts 2 and 10 were used for the through-hardening of fatty acid. The fatty acid used had the iodine value of 88.1 and an acid value of 202.0. It had the following composition:

$C_{18:2}$: 14.5 wt %

$C_{18:1}$: 77.5 wt %

Balance: saturated fatty acids with differing chain length

The acid value (AV) is used for determining the content of free organic acids in fats (procedure see Deutshes Arzneibuch, 7th edition, 1968) and is a measure of the selectivity of the hardening. The acid number should remain as constant as possible during the hardening. Only the iodine value (IV) as a test value for the unsaturated fatty acids content in fats should be reduced. The aim of the industrial hardening is the reduction of the iodine value to values below 1 in order to improve colour, smell and thermal stability.

TABLE 5

Dependence of the activity and cis/trans-isomerisation on the space velocity during the supercritical hydrogenation with Pd/OFP

| Cat. no. | Catalyst designation/particle size | LHSV [$h^{-1}$] | Hydrogenating activity A | IV decrease [$h^{-1}$] | specific IV decrease [l/h × g am] | cis/trans-isomerisation B | Reaction parameters |
| --- | --- | --- | --- | --- | --- | --- | --- |
| 2 | 1% Pd/OFP 0.4–0.8 mm | 5 | 6.7 | 526 | 95636 | 0.161 | 60° C., 100 bar $CO_2$ + superstoichiometric $H_2$ linoleic acid ethyl ester |
| 2 | 1% Pd/OFP 0.4–0.8 mm | 10 | 14.3 | 1151 | 209273 | 0.105 | 60° C., 100 bar $CO_2$ + superstoichiometric $H_2$ linoleic acid ethyl ester |
| 2 | 1% Pd/OFP 0.4–0.8 mm | 15 | 22.8 | 1821 | 331091 | 0.078 | 60° C., 100 bar $CO_2$ + superstoichiometric $H_2$ linoleic acid ethyl ester |
| 2 | 1% Pd/OFP 0.4–0.8 mm | 30 | 35.0 | 2581 | 566500 | 0.199 | 60° C., 100 bar $CO_2$ + superstoichiometric $H_2$ linoleic acid ethyl ester |
| 2 | 1% Pd/OFP 0.4–0.8 mm | 60 | 52.3 | 3862 | 847650 | 0.280 | 60° C., 100 bar $CO_2$ + superstoichiometric $H_2$ linoleic acid ethyl ester |

EXAMPLE 4

In a method comparison between the method according to the invention and the traditional trickle bed hardening, catalyst 2 was used for the selective hardening of sunflower oil. The sunflower oil used had the following composition:

$C_{18:3}$: 1 wt %

$C_{18:2}$: 64.8 wt %

$C_{18:1}$: 21.0 wt %

Balance: saturated fatty acids with differing chain length

There was used as supercritical solvent a gas mixture of 75 vol. % carbon dioxide and 25 vol. % propane. The results of this test series are given in Table 6.

The superiority of the method according to the invention is also found in the selective hardening of triglycerides (here: sunflower oil), in terms both of the activity and of the selectivity. The increase in the hydrogenating activity with the space velocity (LHSV) points to the fact that the reaction is not limited by the mass transport. Similar hydrogenating capacities can be achieved as in the selective hardening of linoleic acid ethyl esters (see Table 5).

EXAMPLE 5

In a further method comparison between the method according to the invention and the traditional trickle bed There can be achieved with the Pd/OFP catalyst (see Table 7) in the presence of a supercritical phase hydrogenating activities which are almost three times higher than in the trickle bed phase. The acid value as a test value for the selectivity of the hardening also remains on a higher level in the supercritical hardening, apparently as a result of the significantly lower temperature.

The hydrogenating activities of the Pd/OFP catalyst in the presence of a supercritical phase are 34–79 times higher than in comparison with traditional catalysts (nos 7, 8 and 9) in the trickle bed phase. The acid values cannot be included in this comparison, since fatty acids of different quality with different acid values were used.

With a space velocity (LHSV) also of 6 2 $h^{-1}$ iodine values well below 1 can still be achieved with the 1% Pd/OFP catalyst.

Even with traditional Ni/$SiO_2$ catalysts higher activities and selectivities can be achieved in the presence of a supercritical phase. Critical for this is probably the carrying out of the reaction at far lower temperature, which results in a reduced deactivation through nickel soap formation.

EXAMPLE 6

For the selective hardening of linoleic acid ethyl esters both in the trickle bed phase and in the method according to the invention, a cordierite monolith with an aluminum oxide washcoat and a palladium covering was used. The cell count of the monolity came to 400 CPSI, corresponding to approx. 62 cells/cm$^2$. The monolith used possessed a Pd covering of 78 mg for a catalyst volume of 8.6 ml.

The test results are given in Table 8. There can be achieved with the method according to the invention, at significantly lower temperature, both a higher activity and a higher selectivity (lower cis/trans-isomerization) than in the trickle bed phase.

TABLE 6

Comparison of various catalyst systems in the supercritical and trickle bed hardening of sunflower oil

| Cat. no. | Catalyst designation/ particle size | Hydrogenating activity A | IV decrease [h$^{-1}$] | specific IV decrease [l/h · g am] | cis/trans- isomerisation B | Reaction parameters | Method |
|---|---|---|---|---|---|---|---|
| 2 | 1% Pd/OFP | 14.9 | 1087 | 209900 | 0.27 | 60° C., 100 bar CO$_2$/propane + stoichiometric H$_2$ LHSV 16.7 h$^{-1}$ | according to the invention |
| 2 | 1% Pd/OFP | 21.4 | 1559 | 301100 | 0.21 | see above, LHSV 26.3 h$^{-1}$ | according to the invention |
| 2 | 1% Pd/OFP | 3.5 | 127.4 | 24600 | 0.32 | 60° C., 5 bar H$_2$, LHSV 14.9 h$^{-1}$ | trickle bed |

TABLE 7

Comparison of various catalyst systems in the supercritical and trickle bed hardening for the through-hardening of fatty acids with an initial iodine value of 88.1 and an acid value of 202.0

| Cat. no. | Catalyst designation/particle size | Hydrogenating activity A | IV decrease [l/h] | specific IV decrease [l/h · g am] | Final iodine value | Acid value | Reaction parameters | Method |
|---|---|---|---|---|---|---|---|---|
| 2 | 1% Pd/OFP 0.4–0.8 mm | 7.9 | 458 | 112700 | 0.29 | 200.8 | 120° C., 140 bar CO$_2$, super stoichiometric H$_2$ LHSV 6.2 h$^{-1}$ | according to the invention |
| 2 | 1% Pd/OFP 0.4–0.8 mm | 2.7 | 191 | 42000 | 42.1 | 197.8 | 170° C., 20 bar H$_2$, LHSV 5.0 h$^{-1}$ | trickle bed |
| 10 | 54% Ni/SiO$_2$ 0.45–1.0 mm | 0.03 | 387 | 420 | 22.3 | 198.3 | 120° C., 140 bar CO$_2$, super stoichiometric H$_2$ LHSV 5.0 h$^{-1}$ | according to the invention |
| 10 | 54% Ni/SiO$_2$ 0.45–1.0 mm | 0.01 | 203 | 223 | 23.5 | 197.2 | 170° C., 20 bar H$_2$, LHSV 5.0 h$^{-1}$ | trickle bed |
| 7 | 2% Pd/TiO$_2$ | 0.12 | 57.8 | 2890 | 0.16 | 202.6 | 170° C., 20 bar H$_2$, LHSV 1.07 h$^{-1}$ | according to DE 41 00 502 |
| 8 | 2% Pd/C | 0.23 | 57.2 | 5720 | 0.74 | 203.4 | dist. fatty acid | |
| 9 | 0.5% Pd/Al$_2$O$_3$ | 0.10 | 48 | 9600 | 39 | — | 60° C., 21.1 bar H$_2$, LHSV 1 h$^{-1}$ fatty acid (oleic acid) | according to DOS 23 10 958 |

TABLE 8

Comparison of various catalyst systems in the supercritical and trickle bed hardening

| Cat. no. | Catalyst designation/ particle size | Hydrogenating activity A | IV decrease [h$^{-1}$] | specific IV decrease [l/h · g am] | cis/trans. isomerisation B | Reaction parameters | Method |
|---|---|---|---|---|---|---|---|
| 11 | Pd/monolith | 2.00 | 530 | 6800 | 0.27 | 60° C., 200 bar CO$_2$, super stoichiometric H$_2$ LHSV 10 h$^{-1}$ linoleic acid ethyl ester | according to the invention |
| 12 | Pd/monolith | 1.79 | 472 | 6058 | 0.38 | 170° C., 20 bar H$_2$, LHSV 10 h$^{-1}$ linoleic acid ethyl ester | trickle bed conditions |

We claim:

1. A method for the continuous hydrogenation of a fat, fatty acid or fatty acid ester comprising;
   A) adding a fat, fatty acid, fatty acid ester or mixture thereof, with the hydrogen required for the hydrogenation in a supercritical solvent medium,
   B) hydrogenating said fat, fatty acid, fatty acid ester, or mixture thereof on a catalyst therefor to obtain a reaction product and,
   C) separating the reaction product from said supercritical solvent medium by the expansion of said supercritical solvent medium.

2. Method according to claim 1 wherein;
   said hydrogenation is carried out on said catalyst at temperatures between the critical temperature ($T_{cr}$) of the supercritical medium and $7 \times T_{cr}$ and at pressures between 0.8 times the critical pressure ($P_{cr}$) of the supercritical medium and $6 \times P_{cr}$.

3. Method according to claim 2 wherein;
   (A) said supercritical medium is selected from the group consisting of carbon dioxide, nitrogen monoxide, dinitrogen monoxide, propane, pentane, binary mixtures, and ternary mixtures,
   (B) optionally, a modifier is added to said supercritical fluid medium.

4. Method according to claim 3 wherein;
   (A) said catalyst is on a shaped support and are selected from the group consisting of platinum group metals, nickel, and copper,
   (B) optionally, said catalyst contains a promoter.

5. Method according to claim 4 wherein;
   (A) said support is spherical-shaped and possesses a diameter in the range between 0.1 and 3.0 mm and,
   (B) said platinum group metals are deposited on said support in an outer shell with a thickness of 10 to 40 μm.

6. Method according to claim 5 wherein;
   the material of the said support is selected from the group consisting of organosiloxane polycondensates, organosiloxane amine copolycondensates, polymeric secondary organosiloxane, and polymeric tertiary organosiloxane amine compounds.

7. Method according to claim 3 wherein;
   said catalyst is deposited as a coating on an inert monolithic support element in the form of a foam ceramic or metallic or ceramic honeycomb element.

8. Method according to claim 3 wherein;
   said catalyst is shaped to a monolithic honeycomb element.

9. Method according to claim 6 wherein;
   (A) said supercritical solvent medium contains modifiers and,
   (B) said catalyst contains promoters.

10. A method for controlling the distribution of cis and trans isomers of a fat, fatty acid or fatty acid ester during hydrogenation comprising;
    A) adding a fat, fatty acid, fatty acid ester or mixture thereof, with the hydrogen required for the hydrogenation in a supercritical solvent medium,
    B) hydrogenating said fat, fatty acid, fatty acid ester, or mixture thereof on a catalyst therefor to obtain a reaction product with a high cis/trans isomer ratio and,
    C) separating the reaction product from said supercritical solvent medium by the expansion of said supercritical solvent medium.

* * * * *